United States Patent [19]
Greelis et al.

[11] Patent Number: 5,336,183
[45] Date of Patent: Aug. 9, 1994

[54] INFLATOR

[75] Inventors: John P. Greelis, Aliso Viejo; Richard L. Quick, Trabuco Canyon; Gary M. Woker, Escondido, all of Calif.

[73] Assignee: Imagyn Medical, Inc., Laguna Niguel, Calif.

[21] Appl. No.: 127,801

[22] Filed: Sep. 28, 1993

[51] Int. Cl.$^5$ ............................................. A61M 29/00
[52] U.S. Cl. ...................................... 607/97; 604/121; 604/224
[58] Field of Search .................. 604/97, 99, 100, 121, 604/207–211, 218, 224

[56] References Cited

U.S. PATENT DOCUMENTS

| | | |
|---|---|---|
| 2,874,877 | 9/1956 | Spencer . |
| 4,312,343 | 1/1982 | LeVeen et al. . |
| 4,346,708 | 8/1982 | LeVeen et al. . |
| 4,439,185 | 3/1984 | Lundquist . |
| 4,583,974 | 4/1986 | Kokernak ............................. 604/211 |
| 4,710,172 | 12/1987 | Jacklich et al. . |
| 4,723,938 | 2/1988 | Goodin et al. . |
| 4,740,203 | 4/1988 | Hoskins et al. ....................... 604/97 |
| 4,743,230 | 5/1988 | Nordquest . |
| 5,209,732 | 5/1993 | Lampropoulos et al. ............ 604/99 |
| 5,213,115 | 5/1993 | Zytkovicz et al. ................... 604/224 |
| 5,215,523 | 6/1993 | Williams et al. ..................... 604/97 |

OTHER PUBLICATIONS

"LeVeen Inflator with Pressure Gauge", Medi-tech.

*Primary Examiner*—John D. Yasko
*Assistant Examiner*—Anthony Gutowski
*Attorney, Agent, or Firm*—Gordon L. Peterson

[57] ABSTRACT

An inflator for use with a catheter having an inflatable component wherein the inflator includes a housing having an elongated plunger passage and an elongated gage passage. The housing includes a one piece main body which defines at least major lengths of both of the passages, and the passages extend in generally side-by-side relationship. The housing has a port which communicates with both of the passages and which can be coupled to the inflatable component of the catheter. A plunger is movable longitudinally in the plunger passage and is extendible out of a plunger opening in the plunger passage. A pressure responsive gage member is movable longitudinally in the gage passage and is responsive to pressure of the fluid adjacent the port. An indicator is responsive to the longitudinal position of the gage member to provide an indication of the pressure of the liquid adjacent the port. A releasable lock carried by the housing limits the plunger movement. The lock is retained in a locked position responsive to pressure in the plunger passage.

18 Claims, 2 Drawing Sheets

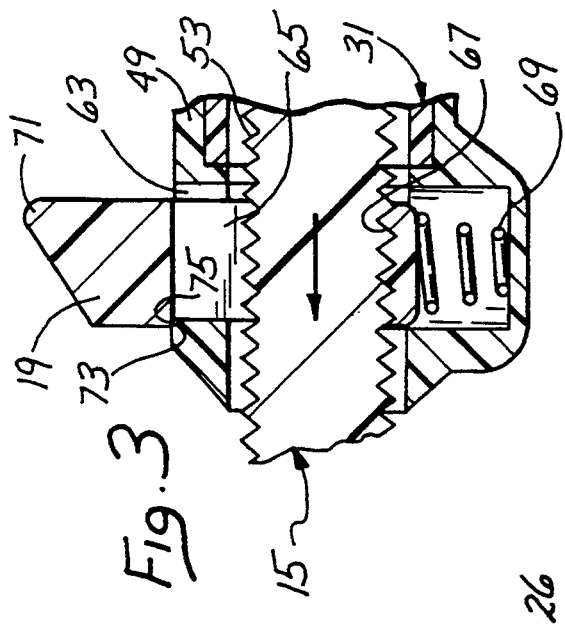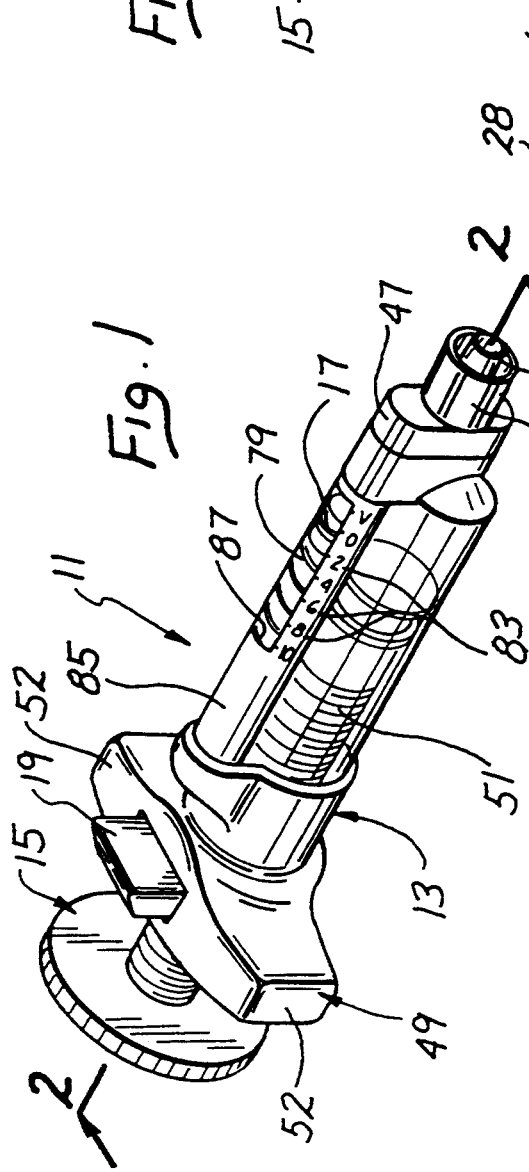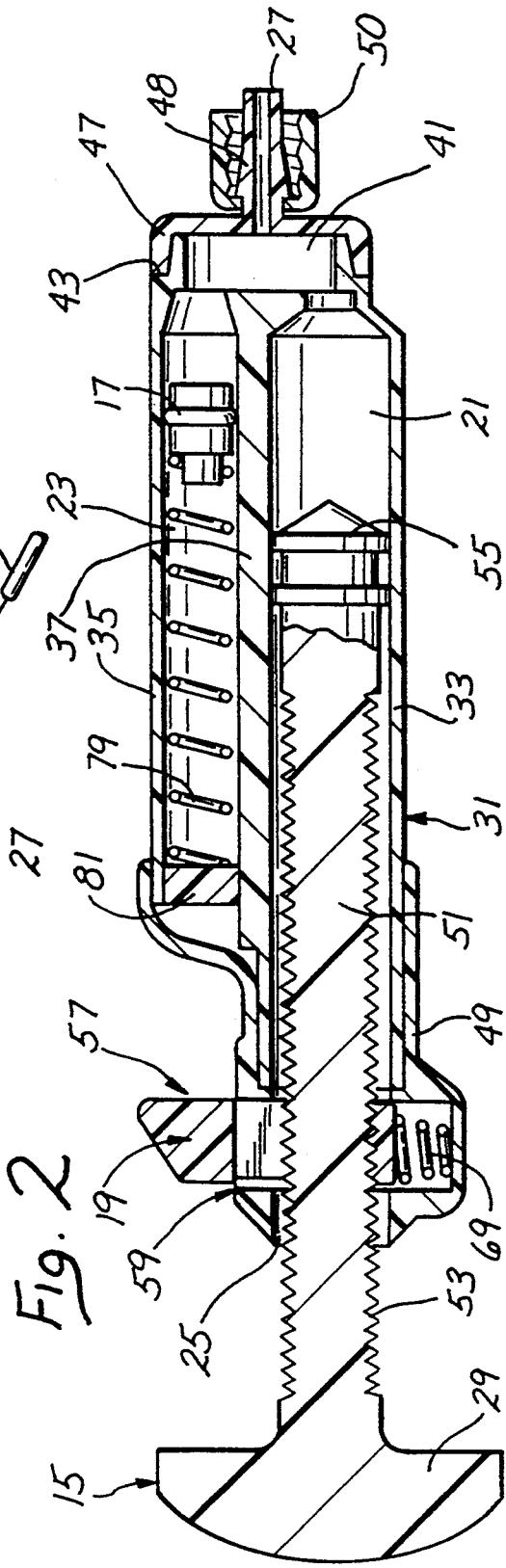

INFLATOR

BACKGROUND OF THE INVENTION

This invention relates to an inflator for use with a catheter having an inflatable component. The inflatable component may include, for example, the balloon of an angioplasty catheter or the balloon or everting element of a linear everting catheter.

Known inflators of this type typically include a housing having a plunger passage and a plunger manually movable in the plunger passage to force fluid out a port of the housing and to the inflatable component of the catheter. The inflatable component of the catheter, in combination with the inflater and any tubing or conduit between these two components, form a closed chamber. In use of the inflater and the catheter, it is important for the physician to know the pressure of the fluid in this closed chamber. To accomplish this, inflators typically include a pressure gage.

One type of pressure gage used with inflators is a circular or dial type pressure gage. Inflators with dial type pressure gages are illustrated, for example, in Nordquest U.S. Pat. No. 4,743,230, Goodin et al U.S. Pat. No. 4,723,938 and Lundquist U.S. Pat. No. 4,439,185.

Linear pressure gages are generally more economical than dial pressure gages. It is known to incorporate a linear pressure gage into the plunger of an inflator as shown, for example, by Leveen et al U.S. Pat. No. 4,346,708. However, the incorporation of a linear pressure gage into the plunger tends to interfere with the manual manipulation of the plunger if the gage is allowed to project from the handle end of the plunger.

SUMMARY OF THE INVENTION

This invention provides an inflator which generally overcomes these disadvantages and provides other important features. This invention utilizes an economical and easily read linear pressure gage which does not interfere with manipulation of the plunger. The cost of the inflator is preferably further reduced through the use of a novel uni-body or one piece main body construction. In addition, the plunger preferably can be positively locked in position.

According to one feature of this invention, the inflator employs a pressure gage which is separate from, and not incorporated in, the plunger. This can be accomplished, for example, by an inflator which includes a housing having an elongated plunger passage and an elongated gage passage with the passages extending generally in side-by-side relationship. This construction provides separate passages for the plunger and gage.

The housing also has a port which communicates with both of the passages and which can be coupled to the inflatable component of the catheter. A plunger is movable longitudinally in the plunger passage and is extendible out of a plunger opening of the plunger passage so that the plunger can be manually moved in the plunger passage. Movement of the plunger in one direction longitudinally in the plunger passage forces a fluid in the plunger passage out of the port so that the inflatable component of the catheter can be inflated. The fluid may be a gas such as air, a liquid such as saline or contrast media or some combination of a gas and a liquid.

A pressure responsive gage member is movable longitudinally in the gage passage and is responsive to pressure of the fluid adjacent the port so that such pressure tends to drive the gage member longitudinally in the gage passage. A biasing member, such as a spring, is provided in the gage passage for resisting such longitudinal movement of the gage member. An indicator is responsive to the longitudinal position of the gage member for providing an indication of the pressure of the fluid adjacent the port. Although the indicator could be a remotely located device to which longitudinal position information of the gage member could be transmitted, preferably the indicator includes indicia on at least one of the housing and the gage member to indicate the pressure of the fluid.

Another important feature of this invention is that the housing preferably includes a one piece main body which defines at least major lengths of both of the plunger passage and the gage passage. These major lengths of the passages extend in generally side-by-side relationship. This one piece main body construction is less expensive to make and to assemble than a construction which might include separate tubes with separate coupling devices for attaching the tubes.

The one piece main body can advantageously be constructed of a relatively inexpensive polymeric material, such as polypropylene, and to facilitate manufacture, the main body may be molded. The polymeric material is preferably transparent or translucent so that the positions of the plunger and gage members within their respective passages can be visually ascertained.

In a preferred construction, the one piece main body includes plunger and gage barrels defining, respectively, the major lengths of the plunger and gage passages and a connecting web for joining the barrels in side-by-side relationship. Although the main body could be a solid block of material containing the plunger and gage passages, the barrel and web construction is preferred because it minimizes the mass of material that is required.

In a preferred construction, the housing also includes first and second end caps coupled to first and second end portions, respectively, of the main body. With this construction, the port is preferably in the first end cap and the plunger opening through which the plunger extends is preferably in the second end cap.

Preferably, the longitudinal position of the plunger in the plunger passage, and hence the pressure of the fluid, can be controlled by rotational and/or translational movement of the plunger. An inflator is operable over a range of pressure conditions and may be required to provide high pressure, such as 300 to 400 psi. It is important that the plunger not undergo retrograde movement in the plunger passage because this would release or reduce the pressure.

Another feature of this invention is to provide a releasably lock carried by the housing for cooperation with the plunger to releasably retain the plunger against translation in the plunger passage and a detent to retain the releasable lock against releasing. Preferably the detent is pressure responsive so that as the pressure provided by the plunger increases, the force tending to hold the detent in a retaining or locking position also increases.

The releasable lock preferably includes a locking member movable generally transversely of the plunger passage and interlockable with the plunger to releasably retain the plunger against translation in the plunger passage. The locking member is movable in a first transverse direction to release the plunger for translation in the plunger passage, and the detent retains the locking member against movement in the first transverse direction.

In a preferred construction, the plunger and the locking member have screw threads whereby the longitudinal position of the plunger can be changed by rotating the plunger and the screw threads are interlockable to retain the plunger against translation. Preferably, the detent includes interlocking portions of the housing and the locking member, and the locking member is movable generally axially in response to pressure in the plunger passage to urge the interlocking portions into interlocking relationship so that the locking member is retained against movement in the first transverse direction, i.e. the releasing direction. The pressure responsive detent preferably includes the plunger in that the pressure of fluid in the plunger passage urges the plunger in a direction to put the interlocking portions in interlocking relationship. Preferably the locking member projects out of the plunger passage and defines a tab which can be manually moved to release the interlocking portions of the housing and the locking member.

The invention, together with additional features and advantages thereof may best be understood by reference to the following description taken in connection with the accompanying illustrative drawings.

BRIEF DESCRIPTIONS OF THE DRAWINGS

FIG. 1 is a perspective view of an inflator constructed in accordance with the teachings of this invention coupled to a catheter which is shown schematically.

FIG. 2 is an enlarged sectional view taken generally along line 2—2 of FIG. 1 with the detent in a releasing position.

FIG. 3 is a fragmentary sectional view taken on the plane of FIG. 2 and illustrating the locking member and portions of the inflator adjacent to the locking member with the detent in a locking position.

DESCRIPTION OF THE PREFERRED EMBODIMENT

Figure 4:
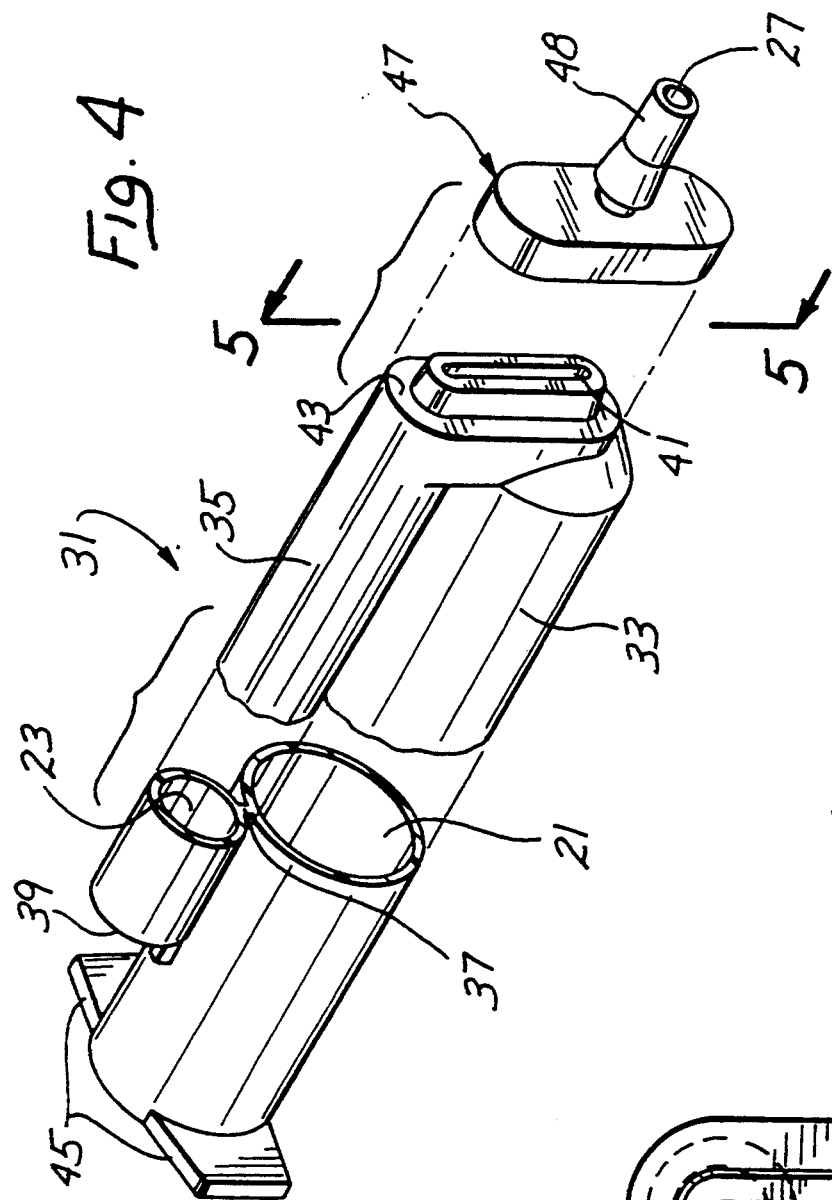
FIG. 4 is a perspective view of one preferred form of the main body and distal end cap of the inflator.
Figure 5:
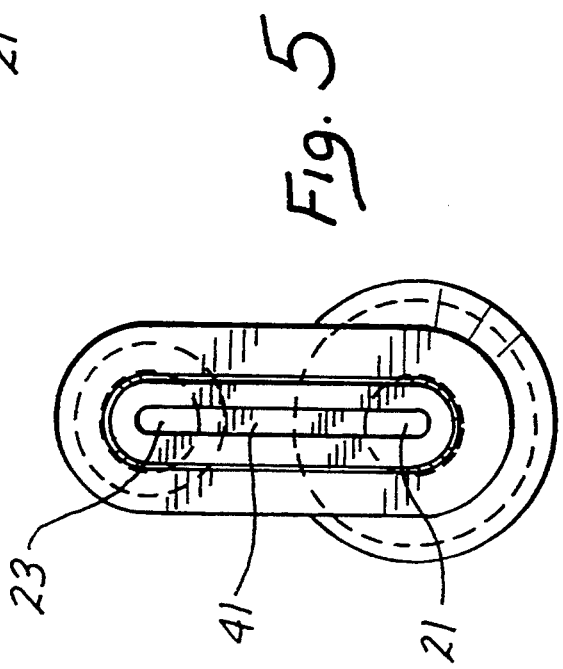
FIG. 5 is an end elevational view of the distal end of the main body.

FIG. 1 shows an inflator 11 which generally comprises a housing 13, a plunger 15, a gage member or piston 17 and a locking member 19. The housing 13 has an elongated plunger passage 21 (FIG. 2) and an elongated gage passage 23 extending in side-by-side relationship with their longitudinal axes parallel. The plunger passage 21 has a plunger opening 25 at a proximal end of the housing 13. The housing 13 also has a port 27 which, in this embodiment, is at a distal end of the housing 13. The port 27 communicates with both of the passages 21 and 23, and it can be coupled to an inflatable component 26 of a catheter 28, such as an angioplasty balloon or an everting element of a linear everting catheter.

The plunger 15 is extendible out of the plunger opening 25 of the plunger passage 21 and provides an enlarged head or handle 29 which can be manually grasped to facilitate manual movement of the plunger in the plunger passage. Movement of the plunger 15 distally or inwardly in the plunger passage 21 forces fluid in the plunger passage out of the port 27 so that the inflatable component 26 of the catheter 28 can be inflated. Conversely, by movement of the plunger 15 proximally or outwardly in the plunger passage 21, the inflatable component 26 of the catheter 28 can be deflated i.e. have its internal pressure reduced. In any event, it is longitudinal movement of the plunger in the plunger passage that brings about a pressure change in the plunger passage.

Preferably, the housing 13 includes a one piece, rigid main body 31 (FIGS. 2 and 4). With this construction, the main body 31 includes a plunger barrel 33, a gage barrel 35 and a thin connecting web 37 joining the barrels in parallel, side-by-side relationship. In this embodiment, the one piece main body 31 is integrally molded as a single, unitary structure from a polymeric material, such as polypropylene. Alternatively, the one piece main body 31 may be molded in two parts separated along the web 39 and bonded together.

In this embodiment, the web 37 extends longitudinally for slightly more than the full length of the gage barrel 35, and the plunger barrel 33 extends proximally of a proximal end 39 of the gage barrel 35. The main body has an oblong chamber 41 at its distal end, which communicates with the passages 21 and 23, and a shoulder 43 surrounding the oblong chamber 41. The main body 31 has tabs 45 at the proximal end of the plunger barrel 33. As shown in FIG. 2, the plunger barrel 33 and the gage barrel 35 define major lengths of the plunger passage 21 and the gage passage 23, respectively. In fact in the illustrated embodiment, the gage barrel 35 provides the full length of the gage passage 23, and the plunger barrel 33 provides almost the full length of the plunger passage 21.

The housing 13 also includes a one-piece distal end cap 47 and a proximal end cap 49 of a suitable rigid polymeric material coupled respectively to the distal and proximal end portions of the main body 31. The port 27 is provided in the distal end cap 47 and the plunger opening 25 is in the proximal end cap 49.

The main body 31 is preferably transparent or translucent, and in this embodiment, the distal end cap 47 is also transparent or translucent and the proximal end cap 49 is opaque. The end caps 47 and 49 are preferably molded of a suitable rigid polymeric material and are bonded or otherwise suitably attached to the main body 31 in any suitable manner such as by an ultrasonic weld and/or an adhesive. The proximal end cap 49 may be molded in two half sections which are bonded together. The distal end cap 47 includes a short axial tube 48, and an internally threaded nut 50 is rotatably mounted on the tube to enable coupling of the inflator 11 at the port 27 to the catheter 28. The proximal end cap 49 has wings 52 (FIG. 1) which receive the tabs 45, respectively, to facilitate the manual grasping of the inflator 11 and the depression or inward movement of the plunger 15.

In this embodiment, the plunger 15 includes a shaft 51 having external screw threads 53 and an elastomeric double seal 55 carried by the distal end of the shaft 51. The seal 55, which may be adhered or mechanically attached to the shaft 51, serves as a piston and provides a fluid tight seal between the plunger 15 and the wall of the plunger passage 21. The shaft 51, which is preferably of one piece integral construction with the handle 29, is preferably constructed of a rigid polymeric material.

A releasable lock 57 is carried by the housing 13 and cooperates with the plunger 15 to releasably retain the plunger against translation in the plunger passage 21. A detent 59 retains the releasable lock 57 against releasing. The lock feature of the invention may be used with or without the other features of this invention.

More specifically, the releasable lock includes the locking member 19 (FIG. 3) which extends radially out of an opening 63 in the proximal end cap 49 and movable generally transversely of the plunger passage 21. The locking member 19 has an axial passage 65 with internal screw threads 67 which are adapted to mate and cooperate with the external screw threads 53 of the plunger 15. A resilient member such as a coil spring 69 acts between the proximal end cap 49 and the locking member 19 to bias the locking member transversely outwardly (upwardly as viewed in FIG. 3) to place the screw threads 53 and 67 in interlocking relationship. This provides two important functions. First, it enables the longitudinal position of the plunger 15 in the plunger passage 21 to be adjusted by rotating of the plunger. Second, it releasably locks or retains the plunger against translation in the plunger passage. The locking member 19 projects through the opening 63 and out of the plunger passage to define a tab 71 which can be manually moved transversely inwardly against the biasing action of the spring 69 to separate the screw threads 53 and 67 to release the plunger 15 for translation in the plunger passage 21.

The detent 59 is provided to prevent retrograde movement of the plunger 15 as a result of high pressure in the plunger passage 21 distally of the seal 55 and/or as the result of unintended transverse movement of the locking member 19 in a direction that would release the plunger 15 for movement. To accomplish this, the detent 59 includes interlocking shoulders or portions 73 and 75 on the locking member 19 and the end cap 49. The shoulders are held in this interlocking relationship as shown in FIG. 3 by the pressure in the plunger passage 21 distally of the seal 55 urging the plunger 15 longitudinally outwardly, i.e. to the left as viewed in FIGS. 2 and 3, and the outward or leftward force is transmitted through the screw threads 53 and 67 to the locking member 19. Thus, the detent 59 is pressure responsive and may be considered as including the plunger 15 in that the plunger directly responds to the pressure of the fluid in the plunger passage 21 and transmits this driving force to the locking member 19. With this arrangement, the higher the pressure in the plunger passage 21 distally of the seal 55, the higher is the force holding the detent 59 in the locked position of FIG. 3. Thus, the locking member 19 is moveable generally axially in response to pressure in the plunger passage 21 to urge the shoulders 73 and 75 into interlocking relationship to retain the locking member 19 against inward transverse movement that would release the plunger 15. To release the detent 59, the tab 71 is pushed forwardly or distally to disengage the shoulders 73 and 75. To release the locking member 19, the locking member 19 is pushed radially inward to disengage the threads 53 and 57.

The pressure gage portion of the inflator 11 includes the gage member or piston 17. The gage member 17 is pressure responsive, movable longitudinally in the gage passage 23 and responsive to pressure of the fluid adjacent the port 27 so that the pressure tends to drive the gage member proximally in the gage passage. A biasing member in the form of a spring 79 acts between the gage member 17 and a plug or spring stop 81 to resiliently resist the longitudinal proximal movement of the gage member 17. The plug 81, which may be of polymeric material, is bonded or otherwise attached to the main body 31 within the proximal end of the gage passage 23 in any suitable manner such as with an adhesive or ultrasonic weld. Alternatively the plug 81 may be attached to the end cap 49.

An indicator in the form of indicia 83 (FIG. 1) is responsive to the longitudinal position of the gage member 17 for providing an indication of the pressure of the liquid adjacent the port 27. The indicia 83 are arranged longitudinally on the main body 31 and may be applied directly to the main body 31 or may be applied to a thin flexible opaque sheet 85 (FIG. 1) which is adhered to the main body around the gage barrel 33. As shown in FIG. 1, the sheet 85 has a longitudinally extending opening 87 along the indicia 83 to expose the gage member 17 so its longitudinal position can be determined in relation to the indicia.

To inflate an inflatable component 26 of the catheter 28, the port 27 is suitably coupled to the catheter, the locking member 19 is depressed and the plunger 15 is advanced into the plunger passage 21 to achieve approximately the desired pressure. The locking member 19 is then released to allow the spring 69 to reestablish interlocking engagement of the threads 53 and 67 so that fine adjustment of the pressure at the port 27 and within the inflatable component 26 can be finely adjusted by rotating of the plunger 15 to advance or retract the plunger to achieve the desired pressure. The plunger passage 21 and the gage passage 23 are both in communication with the port 27 so that the gage member 17 is exposed to the same pressure. This pressure moves the gage member 17 longitudinally and proximally in the gage passage 23 against the biasing force of the spring 79, and the location of the gage member 17 in relation to the indicia 83 can be ascertained through the opening 87 (FIG. 1). Consequently, the indicia 83 provide an indication of the pressure of fluid adjacent the port 27.

The pressure in the plunger passage 21 distally of the seal 55 applies a force to the plunger 15 tending to urge it to the left as viewed in FIGS. 2 and 3 thereby placing the shoulder 73 (FIG. 3) over the shoulder 75 and into interlocking engagement with the shoulder 75. This prevents radial inward movement of the locking member 19. To allow the locking member 19 to move radially inwardly, the user must first push the tab 71 forwardly to disengage the shoulders 73 and 75.

Although an exemplary embodiment of the invention has been shown and described, many changes, modifications and substitutions may be made by one having ordinary skill in the art without necessarily departing from the spirit and scope of this invention.

We claim:

1. An inflator for use with a catheter having an inflatable component, said inflator comprising:

a housing having an elongated plunger passage and an elongated gage passage, said passages extending generally in side-by-side relationship, said plunger passage having a plunger opening;

said housing having a port which communicates with both of said passages and which can be coupled to the inflatable component of the catheter;

a plunger movable longitudinally in said plunger passage and extendible out of the plunger opening of the plunger passage whereby the plunger can be manually moved in the plunger passage, movement of the plunger in one direction longitudinally in the plunger passage forcing a fluid in the plunger passage out of said port whereby the inflatable component of the catheter can be inflated;

a pressure responsive gage member movable longitudinally in said gage passage and responsive to pressure of the fluid adjacent the port whereby such pressure tends to drive the gage member longitudinally in the gage passage;

a biasing member for resisting such longitudinal movement of the gage member; and an indicator responsive to the longitudinal position of the gage member for providing an indication of the pressure of the fluid adjacent the port.

2. An inflator as defined in claim 1 wherein the indicator includes indicia on at least one of the housing and the gage member.

3. An inflator for use with a catheter having an inflatable component, said inflator comprising:

a housing having an elongated plunger passage and an elongated gage passage, said housing including a one piece main body which defines at least major lengths of both of said passages, said major lengths of said passages extending in generally side-by-side relationship, said plunger passage having a plunger opening;

said housing having a port which communicates with both of said passages and which can be coupled to the inflatable component of the catheter;

a plunger movable longitudinally in said plunger passage and extendible out of the plunger opening of the plunger passage whereby the plunger can be manually moved in the plunger passage, movement of the plunger in one direction longitudinally in the plunger passage forcing a fluid in the plunger passage out of said port whereby the inflatable component of the catheter can be inflated;

a pressure responsive gage member movable longitudinally in said gage passage and responsive to pressure of the fluid adjacent the port whereby such pressure tends to drive the gage member longitudinally in the gage passage;

a biasing member for resisting such longitudinal movement of the gage member; and an indicator responsive to the longitudinal position of the gage member for providing an indication of the pressure of the fluid adjacent the port.

4. An inflator as defined in claim 3 wherein said main body is constructed of a polymeric material.

5. An inflator as defined in claim 3 wherein said main body is integrally molded as a single, unitary structure from polymeric material.

6. An inflator as defined in claim 3 wherein said main body is molded from a polymeric material.

7. An inflator as defined in claim 3 wherein said main body includes plunger and gage barrels defining respectively, said major lengths of the plunger and gage passages and a connecting web for joining said barrels in side-by-side relationship.

8. An inflator as defined in claim 3 wherein said main body is constructed of a polymeric material, the main body has a distal end portion and the housing includes an end cap of polymeric material joined to the distal end portion of the main body, said port being in said end cap.

9. An inflator as defined in claim 3 wherein said main body has first and second end portions and said housing includes first and second end caps coupled to said first and second end portions, respectively, of said main body, said port is in said first end cap and said plunger opening is in said second end cap.

10. An inflator as defined in claim 3 including a releasable lock carried by the housing for cooperation with the plunger to releasably retain the plunger against translation in the plunger passage.

11. An inflator as defined in claim 10 including a detent means on said housing and lock for retaining the releasable lock against releasing.

12. An inflator as defined in claim 11 wherein the releasable lock includes a member for releasably retaining the plunger against translation in the plunger passage and movable in a first direction to release the plunger for translation in the plunger passage and the detent means is responsive to pressure in the plunger passage to retain the member against movement in said first direction.

13. An inflator for use with a catheter having an inflatable component, said inflator comprising:

a housing having a plunger passage opening at a plunger opening and a port communicating with the plunger passage, said port being couplable to the inflatable component of the catheter;

a plunger movable in said plunger passage and extendible out of the plunger opening in the plunger passage whereby the plunger can be manually moved in the plunger passage, movement of the plunger in one direction longitudinally in the plunger passage forcing a fluid in the plunger passage out of said port whereby the inflatable component of the catheter can be inflated;

a pressure gage on the housing for providing an indication of the pressure of the fluid adjacent the port;

a releasable lock carried by the housing for cooperation with the plunger to releasably retain the plunger against translation in the plunger passage, said releasable lock being movable in response to pressure in the plunger passage; and a pressure responsive detent on said housing and lock to retain the releasable lock against releasing.

14. An inflator as defined in claim 13 wherein the releasable lock includes a locking member movable generally transversely of the plunger passage and interlockable with the plunger to releasably retain the plunger against translation in the plunger passage, said locking member being movable in a first transverse direction to release the plunger for translation in the plunger passage, and the pressure responsive detent retains the locking member against movement in the first transverse direction.

15. An inflator as defined in claim 14 wherein the plunger and the locking member have screw threads whereby the longitudinal position of the plunger can be changed by rotating the plunger and said screw threads are interlockable to retain the plunger against translation.

16. An inflator as defined in claim 15 wherein the pressure responsive detent includes interlocking portions of the housing and the locking member and the locking member is movable generally axially in response to pressure in the plunger passage to urge the interlocking portions into interlocking relationship whereby the locking member is retained against movement in the first transverse direction.

17. An inflator as defined in claim 16 wherein the locking member projects out of the plunger passage and defines a tab which can be manually moved to release the interlocking portions of the housing and the locking member.

18. An inflator as defined in claim 16 wherein the pressure responsive detent includes said plunger whereby pressure of fluid in the plunger passage urges the plunger in a direction to put said interlocking portions in interlocking relationship.

* * * * *